(12) United States Patent  
Bou Chedid et al.

(10) Patent No.: US 8,927,712 B2
(45) Date of Patent: Jan. 6, 2015

(54) PROCESS FOR THE PREPARATION OF A MONO-N-ALKYLPIPERAZINE

(71) Applicant: BASF SE, Ludwigshafen (DE)

(72) Inventors: Roland Bou Chedid, Mannheim (DE); Johann-Peter Melder, Böhl-Iggelheim (DE); Ulrich Abel, Schifferstadt (DE); Roman Dostalek, Neuleiningen (DE); Bernd Stein, Alsbach-Hähnlein (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/906,931

(22) Filed: May 31, 2013

(65) Prior Publication Data

US 2013/0324731 A1  Dec. 5, 2013

Related U.S. Application Data

(60) Provisional application No. 61/654,132, filed on Jun. 1, 2012.

(51) Int. Cl.
| | |
|---|---|
| *C07D 241/04* | (2006.01) |
| *C07D 295/00* | (2006.01) |
| *C07D 295/088* | (2006.01) |
| *B01J 23/83* | (2006.01) |
| *B01J 35/02* | (2006.01) |
| *B01J 37/00* | (2006.01) |
| *B01J 37/03* | (2006.01) |
| *C07D 295/03* | (2006.01) |
| *B01J 37/08* | (2006.01) |
| *B01J 37/18* | (2006.01) |

(52) U.S. Cl.
CPC ............ *C07D 295/088* (2013.01); *B01J 23/83* (2013.01); *B01J 35/023* (2013.01); *B01J 37/0009* (2013.01); *B01J 37/031* (2013.01); *C07D 295/03* (2013.01); *B01J 37/08* (2013.01); *B01J 37/18* (2013.01); *B01J 2523/00* (2013.01)
USPC .......................................... 544/404; 544/398

(58) Field of Classification Search
CPC .................................................. C07D 295/03
See application file for complete search history.

(56) References Cited

U.S. PATENT DOCUMENTS

| | | |
|---|---|---|
| 3,166,558 A | 1/1965 | Mascioli |
| 3,275,554 A | 9/1966 | Wagenaar |
| 3,751,475 A | 8/1973 | van der Voort et al. |
| 3,997,368 A | 12/1976 | Petroff et al. |
| 4,014,933 A | 3/1977 | Boettger et al. |
| 4,323,550 A | 4/1982 | Goupil |
| 4,442,306 A | 4/1984 | Mueller et al. |
| 4,739,051 A | 4/1988 | Schroeder et al. |
| 4,832,702 A | 5/1989 | Kummer et al. |
| 4,845,218 A | 7/1989 | Schroeder |
| 4,851,578 A | 7/1989 | Fischer et al. |
| 4,851,580 A | 7/1989 | Mueller et al. |
| 4,910,304 A | 3/1990 | Fischer et al. |
| 5,002,922 A | 3/1991 | Irgang et al. |
| 5,110,928 A | 5/1992 | Schroeder et al. |
| 5,463,130 A | 10/1995 | Witzel et al. |
| 5,530,127 A | 6/1996 | Reif et al. |
| 5,847,131 A | 12/1998 | Simon et al. |

(Continued)

FOREIGN PATENT DOCUMENTS

| | | |
|---|---|---|
| CA | 1046166 A1 | 1/1979 |
| CA | 1055677 A1 | 6/1979 |

(Continued)

OTHER PUBLICATIONS

U.S. Appl. No. 13/906,960, filed May 31, 2013.
U.S. Appl. No. 13/910,554, filed Jun. 5, 2013.
U.S. Appl. No. 13/910,602, filed Jun. 5, 2013.
Database WPI, Week 198731, Thomson Scientific, London, GA; AN 1987-218358 (XP002664153), & JP 62 145076 A (KOA Corp) Jun. 29, 1987.
International Search Report for PCT/EP2011/059848—Jun. 14, 2011, dated Jul. 25, 2011.
International Search Report for PCT/EP2011/067612 dated Nov. 22, 2011.
International Search Report for PCT/EP2011/068700, mailed Feb. 17, 2012.

*Primary Examiner* — Noble Jarrell
*Assistant Examiner* — John S Kenyon
(74) *Attorney, Agent, or Firm* — Drinker Biddle & Reath LLP

(57) ABSTRACT

Process for the preparation of a mono-N-alkylpiperazine of the formula I

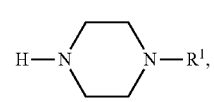

in which $R^1$ is $C_1$- to $C_5$-alkyl or 2-(2-hydroxyethoxy)ethyl, by reacting diethanolamine (DEOA) of the formula II

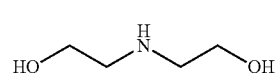

with a primary amine of the formula $H_2N-R^1$ (III) in the presence of hydrogen and a catalyst molding, where the reaction is carried out in the liquid phase at an absolute pressure in the range from 150 to 250 bar and the amination is carried out by means of a catalyst molding, the precursor of which can be prepared according to a process in which (i) an oxidic material comprising copper oxide, aluminum oxide and lanthanum oxide is provided,
(ii) pulverulent metallic copper and/or copper flakes and optionally graphite is added to the oxidic material,
(iii) the mixture resulting from step ii is shaped to give a molding, where the oxidic material is obtainable by simultaneous or successive precipitation of the component copper oxide, of the component aluminum oxide and of the component lanthanum oxide and subsequent drying and calcination and, after the shaping according to step iii, the catalyst molding is calcined again.

34 Claims, No Drawings

(56) References Cited

U.S. PATENT DOCUMENTS

| | | |
|---|---|---|
| 6,187,957 B1 | 2/2001 | Meyer et al. |
| 6,448,457 B1 | 9/2002 | Hesse et al. |
| 7,750,189 B2 * | 7/2010 | Kubanek et al. ............. 564/480 |
| 8,436,169 B2 | 5/2013 | Wigbers et al. |
| 8,450,530 B2 | 5/2013 | Mueller et al. |
| 2003/0089591 A1 | 5/2003 | Wolfert et al. |
| 2005/0000791 A1 | 1/2005 | Wolfert et al. |
| 2007/0232833 A1 | 10/2007 | Haese et al. |
| 2008/0064882 A1 | 3/2008 | Huber-Dirr et al. |
| 2008/0255351 A1 | 10/2008 | Hoffer et al. |
| 2008/0299390 A1 | 12/2008 | Houssin et al. |
| 2009/0286977 A1 | 11/2009 | Kubanek et al. |
| 2010/0069681 A1 * | 3/2010 | Heimann et al. ............. 568/678 |
| 2010/0274010 A1 | 10/2010 | Kubanek et al. |
| 2010/0274055 A1 | 10/2010 | Kubanek et al. |
| 2011/0054167 A1 | 3/2011 | Kubanek et al. |
| 2011/0137029 A1 | 6/2011 | Kubanek et al. |
| 2011/0137030 A1 | 6/2011 | Kubanek et al. |
| 2011/0172430 A1 | 7/2011 | Ernst et al. |
| 2011/0218270 A1 | 9/2011 | Suter et al. |
| 2011/0218323 A1 | 9/2011 | Dahmen et al. |
| 2011/0251433 A1 | 10/2011 | Wigbers et al. |
| 2011/0288337 A1 | 11/2011 | Chedid et al. |
| 2011/0288338 A1 | 11/2011 | Wigbers et al. |
| 2011/0294977 A1 | 12/2011 | Schaub et al. |
| 2012/0035049 A1 | 2/2012 | Kubanek et al. |
| 2012/0035399 A1 | 2/2012 | Abillard et al. |
| 2012/0095221 A1 | 4/2012 | Wigbers et al. |
| 2012/0157679 A1 | 6/2012 | Wigbers et al. |
| 2013/0331573 A1 * | 12/2013 | Bou Chedid et al. ......... 544/358 |

FOREIGN PATENT DOCUMENTS

| | | |
|---|---|---|
| CN | 102101847 A | 6/2011 |
| CN | 102304101 A | 1/2012 |
| DE | 917 784 C | 9/1954 |
| DE | 941 909 C | 4/1956 |
| DE | 1954546 A1 | 5/1971 |
| DE | 21 25039 A1 | 12/1971 |
| DE | 1953263 A1 | 2/1972 |
| DE | 2445303 A1 | 4/1976 |
| DE | 26 28 087 A1 | 1/1977 |
| DE | 2706826 A1 | 9/1977 |
| DE | 36 11 230 A1 | 10/1987 |
| DE | 4021230 | 1/1991 |
| DE | 4028295 A1 | 3/1992 |
| DE | 19809418 A1 | 9/1999 |
| DE | 19859776 A1 | 6/2000 |
| DE | 10218849 A1 | 11/2003 |
| EP | 70 512 A1 | 1/1983 |
| EP | 75940 A1 | 4/1983 |
| EP | 0137478 A2 | 4/1985 |
| EP | 0227904 A1 | 7/1987 |
| EP | 235651 A1 | 9/1987 |
| EP | 0257443 A1 | 3/1988 |
| EP | 382049 A1 | 8/1990 |
| EP | 0434062 A1 | 6/1991 |
| EP | 440829 A1 | 8/1991 |
| EP | 446783 A2 | 9/1991 |
| EP | 514 692 A2 | 11/1992 |
| EP | 552 463 A1 | 7/1993 |
| EP | 599 180 A1 | 6/1994 |
| EP | 673 918 A1 | 9/1995 |
| EP | 696572 A1 | 2/1996 |
| EP | 0816350 A1 | 1/1998 |
| EP | 1 312 599 A1 | 5/2003 |
| EP | 1 312 600 A1 | 5/2003 |
| GB | 1512797 A | 6/1978 |
| JP | 62145076 A | 6/1987 |
| WO | WO-92/04119 A1 | 3/1992 |
| WO | WO-03/051508 A1 | 6/2003 |
| WO | WO-2004/085356 A1 | 10/2004 |
| WO | WO-2005/110969 A1 | 11/2005 |
| WO | WO-2006/005505 A1 | 1/2006 |
| WO | WO-2006/114417 A2 | 11/2006 |
| WO | WO-2007/036496 A1 | 4/2007 |
| WO | WO-2008/006750 A1 | 1/2008 |
| WO | WO-2008/006754 A1 | 1/2008 |
| WO | WO-2009/027249 A2 | 3/2009 |
| WO | WO-2009/080506 A1 | 7/2009 |
| WO | WO-2009/080507 A1 | 7/2009 |
| WO | WO-2009/080508 A1 | 7/2009 |
| WO | WO-2010/031719 A1 | 3/2010 |
| WO | WO-2010/052181 A2 | 5/2010 |
| WO | WO-2010/054988 A2 | 5/2010 |
| WO | WO-2010/069856 A1 | 6/2010 |
| WO | WO-2010/089265 A2 | 8/2010 |
| WO | WO-2010/089266 A2 | 8/2010 |
| WO | WO-2010/089346 A2 | 8/2010 |
| WO | WO-2010/103062 A1 | 9/2010 |
| WO | WO-2010/106133 A1 | 9/2010 |
| WO | WO-2010115759 A2 | 10/2010 |
| WO | WO-2010/146009 A1 | 12/2010 |
| WO | WO-2011/067200 A1 | 6/2011 |
| WO | WO-2011067199 A1 | 6/2011 |
| WO | WO-2011/082967 A1 | 7/2011 |
| WO | WO-2011/082994 A1 | 7/2011 |
| WO | WO-2011/107512 A1 | 9/2011 |
| WO | WO-2011/115759 A1 | 9/2011 |
| WO | WO-2011157710 A1 | 12/2011 |
| WO | WO-2012049101 A1 | 4/2012 |

* cited by examiner

PROCESS FOR THE PREPARATION OF A MONO-N-ALKYLPIPERAZINE

CROSS-REFERENCE TO RELATED APPLICATIONS

This application claims benefit (under 35 USC 119(e)) of U.S. Provisional Application 61/654,132, filed Jun. 1, 2012, which is incorporated by reference.

The present invention relates to a process for the preparation of a mono-N-alkylpiperazine of the formula I

in which $R^1$ is $C_1$- to $C_5$-alkyl or 2-(2-hydroxyethoxy)ethyl, by reacting diethanolamine (DEOA) of the formula II

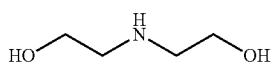

with a primary amine of the formula $H_2N-R^1$ (III) in the presence of hydrogen and a catalyst molding.

The process products are used inter alia as intermediates in the production of fuel additives (U.S. Pat. No. 3,275,554 A; DE 21 25 039 A and DE 36 11 230 A), surfactants, drugs and crop protection agents, hardeners for epoxy resins, catalysts for polyurethanes, intermediates for producing quaternary ammonium compounds, plasticizers, corrosion inhibitors, synthetic resins, ion exchangers, textile auxiliaries, dyes, vulcanization accelerators and/or emulsifiers.

WO 2011/067199 A1 (BASF SE) relates to certain aluminum oxide-, copper-, nickel-, cobalt- and tin-containing catalysts and their use in processes for the preparation of an amine from a primary or secondary alcohol, aldehyde and/or ketone. The preparation of N-methylpiperazine from DEOA and monomethylamine is mentioned in general terms on page 25, lines 20-21.

WO 2011/157710 A1 (BASF SE) describes the preparation of certain cyclic tertiary methylamines, where an amino alcohol from the group 1,4-aminobutanol, 1,5-aminopentanol, aminodiglycol (ADG) or aminoethylethanolamine is reacted with methanol at elevated temperature in the presence of a copper-containing heterogeneous catalyst in the liquid phase.

WO 2012/049101 A1 (BASF SE) relates to a process for the preparation of certain cyclic tertiary amines by reacting an amino alcohol from the group 1,4-aminobutanol, 1,5-aminopentanol, aminodiglycol (ADG) or aminoethylethanolamine with a certain primary or secondary alcohol at elevated temperature in the presence of a copper-containing heterogeneous catalyst in the liquid phase.

CN 102 101 847 A (Zhangjiagang Tianyou New Material Techn. Co., Ltd.) describes a two-stage synthesis for N-methyl-N-(2-chloroethyl)piperazine from aminodiglycol (ADG) via N-methylpiperazine as intermediate.

CN 102 304 101 A (Shaoxing Xingxin Chem. Co., Ltd.) relates to the simultaneous preparation of piperazine and N-alkylpiperazines by reacting N-hydroxyethyl-1,2-ethanediamine with primary $C_{1-7}$-alcohols in the presence of metallic catalysts.

EP 446 783 A2 (BASF AG) relates inter alia to the preparation of N-aryl-substituted piperazines by amination of corresponding N,N-di(2-hydroxyalkyl)-N-arylamines.

EP 235 651 A1 (BASF AG) teaches a process for the preparation of N-methylpiperazine from DEOA and methylamine in the presence of metal-containing supported catalysts, in particular Cu-containing catalysts.

DE 198 59 776 A1 (BASF AG) relates to certain amination processes using catalyst moldings which comprise oxygen-containing compounds of titanium and of copper and metallic copper.

WO 04/085356 A1 and WO 2010/115759 A2 (both BASF AG) describe the use of certain $Al_2O_3$/Cu/lanthanum oxide catalysts for the hydration of certain carbonyl compounds.

The object of the present invention was to improve the economic feasibility of processes to date for the preparation of mono-N-alkylpiperazines of the formula I and to overcome one or more disadvantages of the prior art. The aim was to find conditions which can be established in technical terms in a simple manner and which make it possible to carry out the process with high conversion, high yield, space-time yields (STY), selectivity coupled with simultaneously high mechanical stability of the catalyst molding and low "runaway risk".

[Space-time yields are given in "amount of product/(catalyst volume·time)" (kg/($l_{cat}$·h)) and/or "amount of product/(reactor volume·time)" (kg/($l_{reactor}$·h))].

Accordingly, a process for the preparation of a mono-N-alkylpiperazine of the formula I

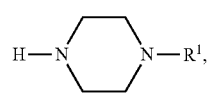

in which $R^1$ is $C_1$- to $C_5$-alkyl or 2-(2-hydroxyethoxy)ethyl, by reacting diethanolamine (DEOA) of the formula II

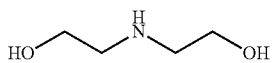

with a primary amine of the formula $H_2N-R^1$ (III) in the presence of hydrogen and a catalyst molding has been found, wherein the reaction is carried out in the liquid phase at an absolute pressure in the range from 150 to 250 bar and the amination is carried out by means of a catalyst molding, the precursor of which can be prepared according to a process in which (i) an oxidic material comprising copper oxide, aluminum oxide and lanthanum oxide is provided,
(ii) pulverulent metallic copper and/or copper flakes and optionally graphite is added to the oxidic material,
(iii) the mixture resulting from ii is shaped to give a molding, where the oxidic material is obtainable by simultaneous or successive precipitation of the component copper oxide, of the component aluminum oxide and of the component lanthanum oxide and subsequent drying and calcination and, after the shaping according to step iii, the catalyst molding is calcined again.

The radical $R^1$ is 2-(2-hydroxyethoxy)ethyl or $C_{1-5}$-alkyl, preferably $C_{1-3}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, particularly preferably methyl, ethyl and 2-(2-hydroxyethoxy)ethyl.

The primary amine III is correspondingly particularly preferably monomethylamine, monoethylamine or 1-amino-2-(2-hydroxyethoxy)ethane (aminodiglycol, ADG).

Preferably preparable with the process according to the invention are amines of the formula I

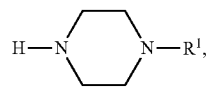

in which $R^1$=methyl, ethyl or 2-(2-hydroxyethoxy)ethyl.

In particular, catalyst moldings are used wherein the oxidic material comprises
(a) copper oxide with a fraction in the range from $50 \leq x \leq 80\%$ by weight, preferably $55 \leq x \leq 75\%$ by weight, in, each case calculated as CuO,
(b) aluminum oxide with a fraction in the range from $15 \leq y \leq 35\%$ by weight, preferably $20 \leq y \leq 30\%$ by weight, and
(c) lanthanum oxide with a fraction in the range from $2 \leq z \leq 20\%$ by weight, preferably $3 \leq z \leq 15\%$ by weight, further preferably $3.5 \leq z \leq 10\%$ by weight,
in each case based on the total weight of the oxidic material after calcination, where: $80 \leq x+y+z \leq 100$, in particular $95 \leq x+y+z \leq 100$.

The process can be carried out continuously or discontinuously. Preference is given to a continuous procedure.

In the circulating-gas procedure, the starting materials (DEOA, the primary amine III) are evaporated in a circulating-gas stream and passed to the reactor in gaseous form.

The starting materials (DEOA, the primary amine III) can also be evaporated as aqueous solutions and be passed with the circulating-gas stream to the catalyst bed.

Preferred reactors are tubular reactors. Examples of suitable reactors with circulating-gas stream can be found in Ullmann's Encyclopedia of Industrial Chemistry, 5th ed., vol. B 4, pages 199-238, "Fixed-Bed Reactors".

Alternatively, the reaction takes place advantageously in a tube-bundle reactor or in a mono-stream plant.

In a mono-stream plant, the tubular reactor in which the reaction takes place can consist of a serial connection of a plurality (e.g. two or three) of individual tubular reactors. Optionally, an intermediate introduction of feed (comprising the DEOA and/or primary amine III and/or $H_2$) and/or circulating gas and/or reactor discharge from a downstream reactor is advantageously possible here.

The circulating-gas amount is preferably in the range from 40 to 1500 m$^3$ (at atmospheric pressure)/[m$^3$ of catalyst (bed volume)·h], in particular in the range from 400 to 1400 m$^3$ (at atmospheric pressure)/[m$^3$ of catalyst (bed volume)·h]. (Atmospheric pressure=1 bar abs.).

The circulating gas comprises preferably at least 10, particularly 50 to 100, very particularly 80 to 100, % by volume of hydrogen ($H_2$).

In preferred embodiments, the catalyst moldings are used in the process according to the invention as unsupported, impregnation, coated or precipitation catalysts.

The catalyst used in the process according to the invention for the amination is notable for the fact that the component copper oxide, the component aluminum oxide and the component lanthanum oxide are precipitated preferably with a sodium carbonate solution, simultaneously or successively, then dried, calcined, shaped, e.g. tableted, and calcined again.

Copper oxide means CuO, $Cu_2O$ or a mixture of both oxides. For quantitative data, copper(I) oxide is calculated as copper(II) oxide.

Aluminum oxide means $Al_2O_3$ and lanthanum oxide means $La_2O_3$.

In particular, the following precipitation method is contemplated:

A) A copper salt solution, an aluminum salt solution and a solution of a salt of lanthanum or a solution comprising copper, aluminum and lanthanum salt is simultaneously, or are successively, precipitated with a sodium carbonate solution.

B) Precipitation of a copper salt solution and, separately, of a solution of a salt of lanthanum or a solution comprising copper salt and a salt of lanthanum onto a prefabricated aluminum oxide support. In one particularly preferred embodiment, this is present in the form of a powder in an aqueous suspension. However, the support material can e.g. also be present as spheres, extrudates, spall or tablets.

In one particular variant of B) (B1), a copper salt solution and a solution of a salt of lanthanum or a solution comprising copper salt and a salt of lanthanum is precipitated preferably with sodium carbonate solution. The initial charge used is an aqueous suspension of the support material aluminum oxide.

Precipitated solids which result from A) or B) are separated off in the usual way, e.g. filtered, and preferably washed to free them from alkali, as is described, for example, in DE 198 09 418 A1 (BASF AG).

After the precipitation of the components, particularly the end products from A) or from B), these are dried at elevated temperature, particularly at temperatures of from 50 to 150° C., preferably at 110 to 130° C. (e.g. over a period from 5 to 30 hours, preferably 10 to 20 hours) and then calcined, preferably e.g. over a period from 0.5 to 6 hours, particularly 1 to 3 hours, at generally 200 to 700° C., in particular at 400 to 650° C.

The starting substances for A) and/or B) can in principle be all Cu(I) and/or Cu(II) salts soluble in the solvents used in the precipitation (preference being given to water), such as, for example, nitrates, carbonates, acetates, oxalates or ammonium complexes, and also analogous ammonium salts and salts of lanthanum. Particular preference is given to using copper (II) nitrate as copper salt. The lanthanum salt used is preferably lanthanum nitrate. The aluminum salt used is preferably aluminum nitrate.

The composition of the oxidic material is preferably such that the fraction of copper oxide is in the range from 50 to 80% by weight, particularly 55 to 75% by weight, in each case calculated as CuO, the fraction of lanthanum oxide is in the range from 2 to 20% by weight, particularly 3 to 15% by weight, and the fraction of aluminum oxide is in the range from 15 to 35% by weight, particularly 20 to 30% by weight, for all components, in each case based on the total weight of the sum of the aforementioned oxidic constituents, these three oxides together constituting at least 80% by weight, particularly at least 95% by weight, of the oxidic material after calcination, where optionally added cement, e.g. clay earth cement, is not included in the oxidic material in the above sense.

In one preferred embodiment, the present invention therefore provides a process, as described above, wherein the oxidic material comprises
(a) copper oxide with a fraction in the range from $50 \leq x \leq 80\%$ by weight, preferably $55 \leq x \leq 75\%$ by weight, in each case calculated as CuO, (b) aluminum oxide with a fraction in the range from 15≤y≤35% by weight, preferably 20≤y≤30% by weight, and (c) lanthanum oxide with a fraction in the range from 2≤z≤20% by weight, preferably 3≤z≤15% by weight, further preferably 3.5≤z≤10% by weight, in each case based on the total weight of the oxidic material after calcination, where: 80≤x+y+z≤100, in particular 95≤x+y+z≤100.

The catalysts used in the process according to the invention are also notable for the fact that the addition of the lanthanum salt during the precipitation leads to a high stability of the ultimately resulting molding which is used as catalyst.

Then (step ii), pulverulent copper and/or copper flakes and optionally graphite is/are added to the oxidic material. Preferably, pulverulent copper and graphite is added. The addition of graphite can also take place before the addition of copper, in which case then preferably a precompaction is firstly carried out. E.g. graphite is added in amounts in the range from 0 to 5% by weight, preferably in the range from 0.5 to 4% by weight, particularly preferably in the range from 0.8 to 2% by weight, in each case based on the total weight of the oxidic material after calcination.

The pulverulent copper used is preferably that which has a grain diameter in the range from 1 to 700 μm, preferably in the range from 5 to 500 μm. Particular preference is given to using a pulverulent copper in which the sieve analysis produces a fraction of particles>500 μm of ≤6%, particularly a fraction of particles>350 μm of ≤5%. The grain morphology is preferably spherical.

The copper flakes used are preferably those which have a D50 value in the range from 5 to 40 μm, particularly in the range from 10 to 35 μm ("D50 value" means that 50% of the particles are smaller than the stated value). Preferably, the sieve analysis produces a fraction of particles>45 μm of ≤6%, particularly ≤2%. The copper flakes preferably have a lamellar flake structure.

Pulverulent copper and/or copper flakes, taken together, are preferably added in amounts in the range from 0.5 to 40% by weight, preferably in the range from 2 to 20% by weight, particularly preferably in the range from 3 to 10% by weight, in each case based on the total weight of the oxidic material after calcination.

In particular embodiments, the oxidic material, in a fraction of at most 10% by weight, preferably at most 5% by weight, based on the total weight of the oxidic material after calcination, can have at least one further component which is selected from the group consisting of oxides of the elements Re, Fe, Ru, Co, Rh, Ir, Ni, Pd and Pt.

Preferably, the catalyst molding comprises no rhenium, no ruthenium, no iron and/or no zinc, in each case neither in metallic (oxidation state=0) nor in ionic (oxidation state≠0), in particular oxidized, form.

Preferably, the catalyst molding comprises no silver and/or molybdenum, in each case neither in metallic (oxidation state=0) nor in ionic (oxidation state≠0), in particular oxidized, form.

Preferably, the catalyst molding comprises no oxygen-containing compounds of silicon, zirconium and/or chromium.

Preferably, the catalyst molding comprises no oxygen-containing compounds of titanium.

In step iii, the mixture resulting from step ii is shaped to give a molding and then calcined. Preference is given to adding graphite to the mixture prior to shaping to give the molding. Preferably, the amount of graphite added is such that the shaping to give a molding can be carried out better. In a preferred embodiment, 0.5 to 5% by weight, particularly 1 to 3% by weight, of graphite, based on the total weight of the mixture resulting from step ii, are added.

The sum of the fractions of oxidic material, metallic copper powder and/or copper flakes and optionally graphite is preferably at least 95% by weight, particularly at least 98% by weight, of the catalyst molding.

The shaping in step iii leads preferably to tablets, rings, ring tablets, extrudates, honeycomb structures or similar moldings. Of suitability for this purpose are all processes known from the prior art.

After the shaping, moldings obtained are then calcined again, at least once. The calcination takes place in each case preferably over a period of in general 0.5 to 10 hours (h), particularly 0.5 to 2.5 hours. The temperature during this at least one calcination step (and also during the optional repeat calcination steps) is generally in the range from 200 to 600° C., preferably in the range from 250 to 500° C. and particularly preferably in the range from 270 to 400° C.

In a further embodiment, the molding obtained can also be treated with boiling water and/or water vapor before it is used for the amination.

In the case of use as catalyst in the oxidic form, the molding is prereduced prior to charging with the starting materials with reducing gases, for example hydrogen, preferably hydrogen/inert gas mixtures, in particular hydrogen/nitrogen mixtures, at elevated temperatures, e.g. in the range from 100 to 500° C., preferably in the range from 150 to 350° C. and in particular in the range from 180 to 200° C. Preference is given here to using a gas mixture with a hydrogen fraction in the range from 1 to 100% by volume, particularly preferably in the range from 1 to 50% by volume.

In a preferred embodiment, the molding is activated prior to being used as a catalyst in a manner known per se by treating with reducing media. The activation takes place either beforehand in a reducing furnace or following insertion in the reactor. If the reactor has been activated beforehand in the reducing furnace, it is incorporated into the reactor and charged directly with the starting materials under hydrogen pressure.

The process according to the invention is preferably carried out continuously, the catalyst preferably being arranged as a fixed bed in the reactor. In this connection, flow through the fixed catalyst bed from above and also from below is possible.

The primary amine III is used preferably in 0.5- to 20-fold molar amount, further preferably in a 2- to 17-fold molar amount, particularly in a 5- to 15-fold molar amount, in particular in a 6- to 14-fold molar amount, further particularly in a 7- to 13-fold molar amount, very particularly in a 8- to 12-fold molar amount, further very particularly in a 8- to 10-fold molar amount, in each case based on the DEOA used.

Particularly preferably, in the case of aminodiglycol (ADG) as primary amine III, the primary amine is used in a 0.5- to 2-fold, in particular in a 0.6- to 1.2-fold, molar amount, in each case based on the DEOA used.

Particularly preferably, in the case of monomethylamine (MMA) as primary amine III, the primary amine is used in a 4- to 13-fold, in particular in a 5- to 12-fold, molar amount, in each case based on the DEOA used.

Particularly preferably, in the case of monoethylamine (MEA) as primary amine III, the primary amine is used in a 2- to 10-fold, in particular in a 3- to 9-fold, molar amount, in each case based on the DEOA used.

The primary amine III can be used as aqueous solution, particularly as 30 to 95% strength by weight aqueous solution, e.g. also 65 to 90% strength by weight aqueous solution.

Monomethylamine and monoethylamine are preferably also used without further solvent (compressed gas, purity particularly 95 to 100% strength by weight).

The starting material DEOA is preferably used as aqueous solution, particularly as 75 to 95% strength by weight aqueous solution, e.g. as 80 to 85% strength by weight aqueous solution.

Preferably, an offgas amount of from 5 to 800 cubic meters (stp)/(cubic meters of catalyst·h), in particular 20 to 300 cubic meters (stp)/(m³ of catalyst·h) is processed. [Cubic meters (stp)=volume converted to standard temperature and pressure conditions (20° C., 1 bar abs.)]. Catalyst volume data always refers to the bulk volume.

The amination of the primary alcohol groups of the starting material DEOA is carried out in the liquid phase. Preferably, the fixed bed process is in the liquid phase.

In the case of the continuous fixed bed process in the liquid phase, the following process configuration, which has inter alia a particularly advantageous effect on the catalyst performance, is particularly preferred. The starting materials (DEOA, primary amine III) including hydrogen are passed over the catalyst firstly at a temperature in the range from 80 to 160° C., preferably 100 to 140° C., particularly preferably 110 to 130° C., and then, e.g. after 1 to 240 min, preferably 5 to 120 min, particularly preferably 10 to 90 min, further particularly preferably 20 to 60 min, the temperature is increased to 180 to 240° C., particularly 180 to 235° C., preferably 185 to 230° C., in particular 190 to 225° C. Accordingly, a start-up procedure at lower temperatures is connected upstream. The reaction product resulting from the start-up procedure can be discarded or returned to the reaction.

When working in the liquid phase, the starting materials (DEOA, primary amine III) are passed, preferably simultaneously, in liquid phase at pressures of from 15.0 to 25.0 MPa (150 to 250 bar), preferably 15.5 to 23.0 MPa, further preferably 16.0 to 22.0 MPa, further preferably 16.5 to 21.5 MPa, particularly preferably 17.0 to 21.0 MPa, and at temperatures of in general 180 to 240° C., particularly 180 to 235° C., preferably 185 to 230° C., in particular 190 to 225° C., including hydrogen over the catalyst, which is usually located in a fixed-bed reaction heated preferably from the outside. Here, both a trickle mode and also a liquid-phase mode is possible. The catalyst hourly space velocity is generally in the range from 0.2 to 0.8, preferably 0.3 to 0.7, particularly preferably 0.4 to 0.6, further preferably 0.4 to 0.5 kg of DEOA per liter of catalyst (bed volume) and per hour (DEOA calculated as 100% strength). Optionally, the starting materials can be diluted with a suitable solvent, such as water, tetrahydrofuran, dioxane, N-methylpyrrolidone or ethylene glycol dimethyl ether. It is expedient to heat the reactants even before they are introduced into the reaction vessel, preferably to the reaction temperature.

The reaction is preferably carried out at a catalyst hourly space velocity in the range from 100 to 1500 liters (stp) of hydrogen/($l_{cat.}$·h), particularly a catalyst hourly space velocity in the range from 400 to 1400 liters of hydrogen (stp)/($l_{cat.}$·h).

[Liters (stp)=l (stp) volume converted to standard temperature and pressure conditions (20° C., 1 bar abs.)]

The pressure in the reaction vessel which arises from the sum of the partial pressures of the primary amine III, of the DEOA and of the reaction products formed, and also optionally of the co-used solvent at the stated temperatures, is expediently increased to the desired reaction pressure by injecting hydrogen.

In the case of continuous operation in the liquid phase, the excess primary amine III can be circulated together with the hydrogen.

If the catalyst is arranged as a fixed bed, it can be advantageous for the selectivity of the reaction to mix the catalyst moldings in the reactor with inert packings, to "dilute" them so to speak. The fraction of packings in such catalyst preparations can be 20 to 80, particularly 30 to 60 and in particular 40 to 50, parts by volume.

The water of reaction formed in the course of the reaction (in each case one mole per mole of reacted alcohol group) generally does not have a disruptive effect on the degree of conversion, the rate of reaction, the selectivity and the service life of the catalyst and is therefore expediently only removed upon working-up the reaction product, e.g. by distillation.

After the reaction discharge has expediently been decompressed, the excess hydrogen and the optionally present excess aminating agents are removed therefrom and the crude reaction product obtained is purified, e.g. by means of fractional rectification. Suitable work-up methods are described e.g. in EP 1 312 600 A and EP 1 312 599 A (both BASF AG). The excess primary amine and the hydrogen are advantageously returned again to the reaction zone. The same applies for any incompletely reacted DEOA.

A work-up of the product of the reaction is preferably as follows:

From the reaction product of the reaction, by means of distillation,
(i) firstly optionally unreacted primary amine III, $R^1$ preferably =$C_1$- to $C_5$-alkyl, is separated off overhead,
(ii) water is separated off overhead,
(iii) optionally present by-products with a lower boiling point than that of the process product 1 (low boilers) are separated off overhead,
(iv) the process product mono-N-alkylpiperazine I is separated off overhead, with optionally present by-products with a higher boiling point than that of the process product 1 (high boilers) and optionally present unreacted DEOA (II) remaining in the bottom.

During the reaction of the process according to the invention, the alkylaminoethylethanolamine of the formula IV

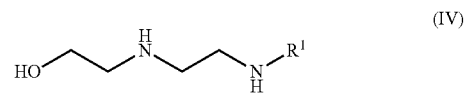

can be formed as by-product:

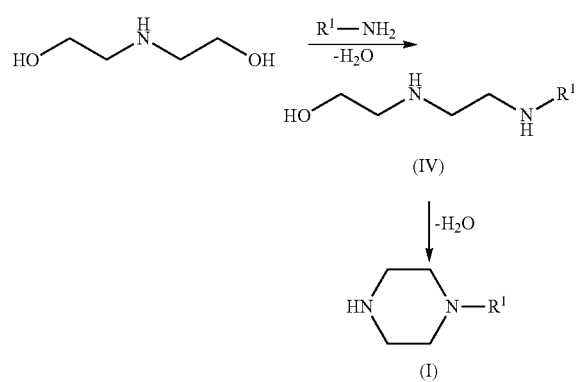

Therefore, in particular by means of distillation,
(v) from the bottom of step iv, optionally present unreacted DEOA (II) and/or optionally present alkylaminoethylethanolamine as by-product with the formula IV are separated off overhead and returned to the reaction.

Primary amine III separated off in step i and having a purity of from 90 to 99.9% by weight, particularly 95 to 99.9% by weight, is preferably returned to the reaction where further preferably some of the separated-off amine III, particularly 1 to 30% by weight of the separated-off amine III, further particularly 2 to 25% by weight of the separated-off amine III, is removed.

A work-up of the product of the reaction of aminodiglycol (ADG), i.e. $R^1$=2-(2-hydroxyethoxy)-ethyl, with DEOA is preferably as follows:

From the reaction product of the reaction, by means of distillation,
(i) firstly water is separated overhead,
(ii) optionally unreacted ADG is separated off overhead,
(iii) optionally present by-products with a lower boiling point than that of the process product I (low boilers) are separated overhead,
(iv) the process product mono-N-alkylpiperazine I is separated off overhead, with optionally present by-products with a higher boiling point than that of the process product 1 (higher boilers) and optionally present unreacted DEOA (II) remaining in the bottom.

In particular, by means of distillation,
(v) from the bottom of step iv, optionally present unreacted DEOA (II) and/or optionally present alkylaminoethylethanolamine as by-product with the formula IV are separated off overhead and returned to the reaction.

ADG separated off in step ii and having a purity of from 90 to 99.9% by weight, particularly 95 to 99.9% by weight, is preferably returned to the reaction where further preferably some of the separated-off ADG, particularly 1 to 30% by weight of the separated-off ADG, further particularly 5 to 25% by weight of the separated-off ADG, is removed.

All pressure data refer to the absolute pressure.
All ppm data refer to the mass.

EXAMPLES

1. Preparation of Catalyst A

A mixture of 13.39 kg of a 19.34% strength copper(II) nitrate solution and 14.78 kg of an 8.12% strength aluminum nitrate solution and 0.56 kg of a 37.58% strength lanthanum nitrate solution (feed material: lanthanum (III) nitrate.6H$_2$O) were dissolved in 1.5 l of water (solution 1). Solution 2 was 60 kg of a 20% strength sodium carbonate solution (feed material: Na$_2$CO$_3$ anhydrous). Solution 1 and solution 2 were passed via separate lines to a precipitation vessel which was provided with a stirrer and comprised 10 l of water heated to 60° C. Here, by means of appropriate adjustment of the feed rates of solution 1 and solution 2, the pH was brought to 6.0.

While keeping the pH constant at 6.0 and the temperature constant at 60° C., the entire solution 1 was reacted with the sodium carbonate solution. The suspension formed in this way was then heated to 80° C., the pH was increased to 8.0 by adding dilute sodium carbonate solution (solution 2), and the mixture was after-stirred for 15 min at this pH and at 80° C. The suspension was filtered and washed with distilled water until the nitrate content of the wash water was <10 ppm.

The filter cake was dried for 16 h at 120° C. and then calcined for 2 h at 600° C. The catalyst powder obtained in this way was precompacted with 1% by weight of graphite. The resulting compacted material was mixed with 5% by weight of Cu flakes, which had a D50 value in the range from 5 to 40 μm (e.g. available from Schlenk Metallpulver GmbH & Co. KG, D-91154 Roth-Barnsdorf), and then with 2% by weight of graphite and compressed to give tablets 3 mm in diameter and 3 mm in height. Finally, the tablets were calcined for 2 h at 350° C.

The catalyst prepared in this way had the chemical composition 61.5% by weight of CuO/28.5% by weight of Al$_2$O$_3$/5.0% by weight of La$_2$O$_3$/5% by weight of Cu (graphite fraction excluded from the calculation).

2. Reaction of DEOA with Monomethylamine (MMA) in a Continuously Operated Tubular Reactor A heated tubular reactor with an internal diameter of 14 mm, a centrally installed thermocouple and a total volume of 1000 ml was filled in the lower section with a bed of glass beads (250 ml), on top of this 500 ml of catalyst A and finally the remainder was filled again with glass beads. Prior to the reaction, the catalyst was activated under atmospheric pressure for 24 hours at max. 200° C. under hydrogen (25 l (stp)/h) (l (stp)=liters at standard temperature and pressure=volume converted to standard temperature and pressure conditions (20° C., 1 bar abs.)). 300 g/h of DEOA (85% strength aqueous), 600 g/h of the primary amine and 200 l (stp)/h of hydrogen were metered through the reactor from bottom to top. The reactor was held at a temperature of approx. 185 to 220° C. and a total pressure of 200 bar. The reaction temperature was selected such that a DEOA conversion of >90% was reached. The mixture leaving the reactor was cooled and decompressed to atmospheric pressure. At various times, samples were taken from the reaction mixture and analyzed by means of gas chromatography. For this, an "RTX-5 Amine" GC column 30 m in length was used, with a temperature program: 70° C./5 min, heat to 280° C. at a rate of 5° C./min, at 280° C./10 minutes. The results of the experiments can be found in table I below.

TABLE I

| Cat. | Pressure bar | H$_2$ l (stp)/ (l · h) | MR MMA:DEOA mol/mol | Temp. ° C. | DEOA feed*) | Hourly space velocity calc. 100% strength DEOA kg/(l · h) | Conversion of DEOA mol % | Sel. NMePIP based on DEOA mol % |
|---|---|---|---|---|---|---|---|---|
| A | 120 | 400 | 8 | 195 | 85% strength | 0.5 | 98 | 73 |
| A | 200 | 400 | 8 | 195 | 85% strength | 0.5 | 97 | 88 |

TABLE I-continued

| Cat. | Pressure bar | $H_2$ l (stp)/ (l·h) | MR MMA:DEOA mol/mol | Temp. °C. | DEOA feed* | Hourly space velocity calc. 100% strength DEOA kg/(l·h) | Conversion of DEOA mol % | Sel. NMePIP based on DEOA mol % |
|---|---|---|---|---|---|---|---|---|
| A | 200 | 400 | 12 | 195 | 85% strength | 0.5 | 97 | 89 |
| A | 200 | 400 | 5 | 195 | 85% strength | 0.5 | 98 | 68 |

Cat.: Catalyst
Temp.: Temperature in the reactor
Hourly space velocity: Catalyst hourly space velocity [kg of DEOA/(liter$_{cat.}$·h)]
MR: Molar ratio in the feed
Sel.: Selectivity
NMePIP: Monomethylpiperazine (N-methyl-PIP)
*)Aqueous solution, in % by weight

3. Reaction of DEOA with Monoethylamine (MEA) in a Continuously Operated Tubular Reactor A heated tubular reactor with an internal diameter of 14 mm, a centrally installed thermocouple and a total volume of 1000 ml was filled in the lower section with a bed of glass beads (250 ml), on top of this 500 ml of catalyst A and finally the remainder was filled again with glass beads. Prior to the reaction, the catalyst was activated under atmospheric pressure for 24 hours at max. 200° C. under hydrogen (25 l (stp)/h) [l (stp)=liters at standard temperature and pressure=volume converted to standard temperature and pressure conditions (20° C., 1 bar abs.)]. 180 g/h of DEOA (85% strength aqueous), 460 g/h of the primary amine and 200 l (stp)/h of hydrogen were metered through the reactor from bottom to top. The reactor was held at a temperature of approx. 185 to 220° C. and a total pressure of 200 bar. The reaction temperature was selected such that a DEOA conversion of >90% was reached. The mixture leaving the reactor was cooled and decompressed to atmospheric pressure. At various times, samples were taken from the reaction mixture and analyzed by means of gas chromatography. For this, an "RTX-5 amine" GC column 30 m in length was used, with a temperature program: 70° C./5 min, heat to 280° C. at a rate of 5° C./min, at 280° C./10 minutes.

The results of the experiments can be found in Table II below.

TABLE II

| Cat. | Pressure bar | $H_2$ l (stp)/ (l·h) | MR MEA:DEOA mol/mol | Temp. °C. | DEOA feed* | Hourly space velocity calc. 100% strength DEOA kg/(l·h) | Conversion of DEOA mol % | Sel. NEtPIP based on DEOA mol % |
|---|---|---|---|---|---|---|---|---|
| A | 200 | 400 | 5 | 217 | 85% strength | 0.4 | 85 | 33 |
| A | 200 | 200 | 5 | 214 | 85% strength | 0.4 | 93 | 39 |
| A | 200 | 200 | 3 | 202 | 85% strength | 0.4 | 79 | 31 |
| A | 200 | 100 | 5 | 200 | 85% strength | 0.2 | 95 | 44 |
| A | 200 | 100 | 9 | 211 | 85% strength | 0.2 | 89 | 40 |
| A | 200 | 400 | 5 | 193 | 85% strength | 0.3 | 82 | 35 |

Cat.: Catalyst

Temp.: Temperature in the reactor

Hourly space velocity: Catalyst hourly space velocity [kg of DEOA/(liter$_{cat.}$·h)]

MR: Molar ratio in the feed

Sel.: Selectivity

NEtPIP: Monoethylpiperazine (N-ethyl-PIP)

*)Aqueous solution, in % by weight

4. Reaction of DEOA with aminodiglycol (ADG, 1-amino-2-(2-hydroxyethoxy)ethane) in a Batch Reactor A batch reactor with stirrer, a thermocouple and a total volume of 300 ml was filled with 7.5 g of activated catalyst. For this, the catalyst was activated under atmospheric pressure for 24 hours at max. 200° C. under hydrogen [25 l (stp)/h] (1 (stp)=liter at standard temperature and pressure=volume converted to standard temperature and pressure conditions (20° C., 1 bar abs.)]. The starting material mixture of DEOA and ADG was initially introduced and the reactor was heated to 180° C. The total reaction mixture was then supplied with 200 bar of hydrogen. At various times, samples were taken from the reaction mixture and analyzed by means of gas chromatography. For this, an "RTX-5 amine" GC column 30 m in length was used, with a temperature program: 70° C./5 min, heat to 280° C. at a rate of 5° C./min, at 280° C./10 minutes. The results of the experiments can be found in Table III below.

TABLE III

| Cat. | Pressure bar | Temp. ° C. | Time (h) | DEOA (g) | MR ADG:DEOA mol/mol | Conversion of DEOA | Conversion of ADG | Sel. HEOEtPIP based on DEOA (mol %) | Sel. HEOEtPIP based on ADG (mol %) |
|---|---|---|---|---|---|---|---|---|---|
| A | 200 | 180 | 5 | 77 | 1 | 43 | 43 | 7 | 8 |
| A | 200 | 180 | 10 | 77 | 1 | 68 | 71 | 16 | 19 |
| A | 200 | 180 | 15 | 77 | 1 | 84 | 86 | 22 | 27 |
| A | 200 | 180 | 20 | 77 | 1 | 93 | 93 | 24 | 31 |
| A | 200 | 180 | 10 | 90 | 0.67 | 74 | 89 | 13 | 25 |
| A | 200 | 180 | 15 | 90 | 0.67 | 89 | 97 | 17 | 29 |

Cat.: Catalyst
Temp.: Temperature in the reactor
MR: Molar ratio in the feed
Sel.: Selectivity (mol %)
Conversion: mol %
HEOEtPIP: 2-(2-Hydroxyethoxy)ethylpiperazine

5. Work-Up

The work-up can preferably take place by means of the following five steps (here using the example of a reaction of DEOA with monomethylamine or monoethylamine):

1) Separating off unreacted primary amine (monomethylamine or monoethylamine) and returning it to the reactor Optionally removal of some of the monomethylamine or monoethylamine from the top of the column.

2) Separating off water

3) Separating off low-boiling secondary components

4) Pure distillation of the N-alkylpiperazine I overhead while separating off high-boiling secondary components via the bottom.

5) Optionally returning some of the high-boiling secondary components, in particular diethanolamine, N—(N'-methyl-2-aminoethyl)ethanolamine, N-methyl-N-(2-aminoethyl)-ethanolamine (or N—(N'-ethyl-2-aminoethyl)ethanolamine, N-ethyl-N-(2-amino-ethyl)ethanolamine) to the reaction.

The invention claimed is:

1. A process for the preparation of a mono-N-alkylpiperazine of the formula I

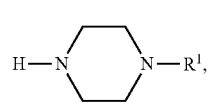

(I)

in which $R^1$ is $C_1$- to $C_5$-alkyl or 2-(2-hydroxyethoxy)ethyl, which comprises reacting diethanolamine (DEOA) of the formula II

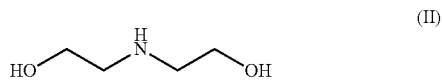

(II)

with a primary amine of the formula $H_2N$—$R^1$ (III) in the presence of hydrogen and a catalyst molding, wherein the reaction is carried out in the liquid phase at an absolute pressure in the range from 150 to 250 bar and the amination is carried out by means of a catalyst molding, the precursor of which can be prepared according to a process in which (i) an oxidic material comprising copper oxide, aluminum oxide and lanthanum oxide is provided, (ii) pulverulent metallic copper and/or copper flakes and optionally graphite is added to the oxidic material, (iii) the mixture resulting from step ii is shaped to give a molding, where the oxidic material is obtainable by simultaneous or successive precipitation of the component copper oxide, of the component aluminum oxide and of the component lanthanum oxide and subsequent drying and calcination and, after the shaping according to step iii, the catalyst molding is calcined again.

2. The process according to claim 1, wherein the oxidic material comprises
   (a) copper oxide with a fraction in the range from $50 \leq x \leq 80\%$ by weight, calculated as CuO,
   (b) aluminum oxide with a fraction in the range from $15 \leq y \leq 35\%$ by weight and
   (c) lanthanum oxide with a fraction in the range from $2 \leq z \leq 20\%$ by weight, in each case based on the total weight of the oxidic material after calcination, where: 80≤x+y+z≤100.

3. The process according to claim 1, wherein the oxidic material comprises
(a) copper oxide with a fraction in the range from 55≤x≤75% by weight, calculated as CuO,
(b) aluminum oxide with a fraction in the range from 20≤y≤30% by weight and
(c) lanthanum oxide with a fraction in the range from 3≤z≤15% by weight,
in each case based on the total weight of the oxidic material after calcination, where: 80≤x+y+z≤100.

4. The process according to claim 1, wherein the oxidic material comprises
(a) copper oxide with a fraction in the range from 55≤x≤75% by weight, calculated as CuO,
(b) aluminum oxide with a fraction in the range from 20≤y≤30% by weight and
(c) lanthanum oxide with a fraction in the range from 3≤z≤15% by weight,
in each case based on the total weight of the oxidic material after calcination, where: 95≤x+y+z≤100.

5. The process according to claim 1, wherein, in step ii, graphite is added in amounts in the range from 0.5 to 5% by weight, based on the total weight of the oxidic material after calcination.

6. The process according to claim 1, wherein pulverulent copper and/or the copper flakes taken together are added in amounts in the range from 0.5 to 40% by weight, based on the total weight of the oxidic material after calcination.

7. The process according to claim 1, wherein 0.5 to 5% by weight of graphite is added to the mixture resulting from step ii prior to the shaping in step iii, based on the total weight of the mixture resulting from step ii.

8. The process according to claim 1, wherein the sum of the fractions of oxidic material, metallic copper powder and/or copper flakes and optionally graphite is at least 95% by weight of the catalyst molding.

9. The process according to claim 1, wherein the catalyst molding comprises no rhenium and/or ruthenium.

10. The process according to claim 1, wherein the catalyst molding comprises no iron and/or zinc.

11. The process according to claim 1, wherein the catalyst molding comprises no oxygen-containing compounds of silicon and/or of zirconium and/or of titanium.

12. The process according to claim 1, wherein the reaction is carried out at a temperature in the range from 180 to 240° C.

13. The process according to claim 1, wherein the reaction is carried out at an absolute pressure in the range from 160 to 220 bar.

14. The process according to claim 1, wherein the primary amine of the formula $H_2N-R^1$ (III) is used in a 5- to 15-fold molar amount, based on the DEOA used.

15. The process according to claim 1, wherein aminodiglycol (ADG) is used in a 0.2- to 2-fold molar amount, based on the DEOA used.

16. The process according to claim 1, wherein monomethylamine (MMA) is used in a 4- to 13-fold molar amount, based on the DEOA used.

17. The process according to claim 1, wherein monoethylamine (MEA) is used in a 2- to 10-fold molar amount, based on the DEOA used.

18. The process according to claim 1, wherein the catalyst is arranged as a fixed bed in the reactor.

19. The process according to claim 1, wherein the reacting diethanolamine (DEOA) of the formula II

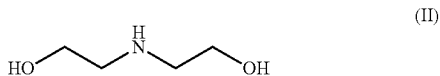

with a primary amine of the formula $H_2N-R^1$ (III) is carried out continuously.

20. The process according to claim 18, wherein the reaction is carried out firstly at a temperature in the range from 80 to 160° C. and then at a temperature in the range from 180 to 240° C.

21. The process according to claim 18, wherein the reaction takes place in a tubular reactor.

22. The process according to claim 18, wherein the reaction takes place in a circulating-gas mode.

23. The process according to claim 1, wherein the DEOA is used as aqueous solution.

24. The process according to claim 1, wherein the primary amine of the formula $H_2N-R^1$ (III) is used as aqueous solution.

25. The process according to claim 1, wherein the reaction is carried out at a catalyst hourly space velocity in the range from 0.3 to 0.7 kg of DEOA/($l_{cat.}$·h).

26. The process according to claim 1, wherein the reaction is carried out at a catalyst hourly space velocity in the range from 400 to 1400 liters (stp) of hydrogen/($l_{cat.}$·h).

27. The process according to claim 1 for the preparation of a mono-N-alkylpiperazine of the formula I in which $R^1$ is methyl, ethyl or 2-(2-hydroxyethoxy)ethyl, by reacting diethanolamine (DEOA) of the formula II with a primary amine of the formula $H_2N-R^1$ (III).

28. A process for the preparation of a mono-N-alkylpiperazine of the formula I

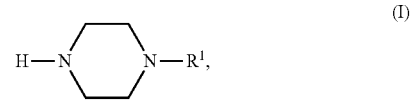

in which $R^1$ is $C_1$- to $C_5$-alkyl or 2-(2-hydroxyethoxy)ethyl,
which comprises reacting diethanolamine (DEOA) of the formula II

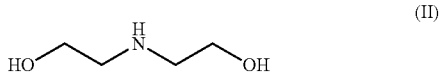

with a primary amine of the formula $H_2N-R^1$ (III) in the presence of hydrogen and a catalyst molding, wherein the reaction is carried out in the liquid phase at an absolute pressure in the range from 150 to 250 bar and the amination is carried out by means of a catalyst molding, the precursor of which can be prepared according to a process in which
(i) an oxidic material comprising copper oxide, aluminum oxide and lanthanum oxide is provided,
(ii) pulverulent metallic copper and/or copper flakes and optionally graphite is added to the oxidic material,
(iii) the mixture resulting from step ii is shaped to give a molding, where the oxidic material is obtainable by simultaneous or successive precipitation of the component copper oxide, of the component aluminum oxide and of the component lanthanum oxide and subsequent drying and calcination and, after the shaping according to step iii, the catalyst molding is calcined again, wherein, from the reaction product of the reaction, by distillation, (i) optionally unreacted primary amine of the formula H₂N—R¹ (III) is separated off overhead, (ii) water is separated off overhead, (iii) optionally present by-products with a lower boiling point than that of the mono-N-alkylpiperazine of the formula I are separated off overhead, (iv) the mono-N-alkylpiperazine of the formula I is separated off overhead, with optionally present by-products with a higher boiling point than that of the mono-N-alkylpiperazine of the formula I and optionally present unreacted DEOA (II) remaining in the bottom.

29. The process according to claim 28, wherein, by distillation, (v) from the bottom of step iv, optionally present unreacted DEOA (II) and/or optionally present alkylaminoethylethanolamine as by-product with the formula IV

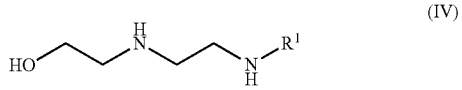

(IV)

are separated off overhead and returned to the reaction.

30. The process according to claim 28, wherein primary amine III separated off in step i and having a purity of from 90 to 99.9% by weight is returned to the reaction.

31. A process for the preparation of a mono-N-alkylpiperazine of the formula I

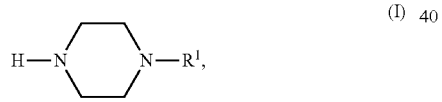

(I)

in which R¹ is 2-(2-hydroxyethoxy)ethyl, which comprises reacting diethanolamine (DEOA) of the formula II

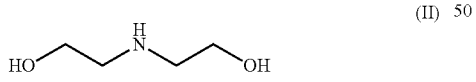

(II)

with a primary amine of the formula H₂N—R¹ (III) in the presence of hydrogen and a catalyst molding, wherein the reaction is carried out in the liquid phase at an absolute pressure in the range from 150 to 250 bar and the amination is carried out by means of a catalyst molding, the precursor of which can be prepared according to a process in which (i) an oxidic material comprising copper oxide, aluminum oxide and lanthanum oxide is provided, (ii) pulverulent metallic copper and/or copper flakes and optionally graphite is added to the oxidic material, (iii) the mixture resulting from step ii is shaped to give a molding, where the oxidic material is obtainable by simultaneous or successive precipitation of the component copper oxide, of the component aluminum oxide and of the component lanthanum oxide and subsequent drying and calcination and, after the shaping according to step iii, the catalyst molding is calcined again, wherein, from the reaction product of the reaction, by distillation (i) water is separated off overhead, (ii) optionally unreacted primary amine III (ADG) is separated off overhead, (iii) optionally present by-products with a lower boiling point than that of the process product I are separated off overhead, (iv) the process product mono-N-alkylpiperazine I is separated off overhead, with optionally present by-products with a higher boiling point than that of the process product I and optionally present unreacted DEOA (II) remaining in the bottom.

32. The process according to claim 31, wherein, by distillation, (v) from the bottom of step iv, optionally present unreacted DEOA (II) and/or optionally present alkylaminoethylethanolamine as by-product with the formula IV

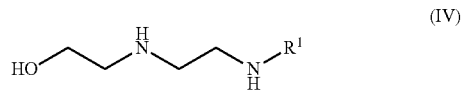

(IV)

are separated off overhead and returned to the reaction.

33. The process according to claim 31, wherein ADG separated off in step ii and having a purity of 90 to 99.9% by weight is returned to the reaction, where some of the ADG is removed.

34. The process according to claim 28, wherein primary amine III separated off in step i and having a purity of from 90 to 99.9% by weight is returned to the reaction, with some of the amine III being removed.

* * * * *